(12) United States Patent
Thomas

(10) Patent No.: US 11,877,984 B1
(45) Date of Patent: Jan. 23, 2024

(54) SALIVA SOLUTION METERING APPARATUS WITH DELIVERY TUBE RETAINING MOUTHPIECE

(71) Applicant: Robert F. Thomas, Key Largo, FL (US)

(72) Inventor: Robert F. Thomas, Key Largo, FL (US)

( * ) Notice: Subject to any disclaimer, the term of this patent is extended or adjusted under 35 U.S.C. 154(b) by 612 days.

(21) Appl. No.: 16/788,839

(22) Filed: Feb. 12, 2020

(51) Int. Cl.
*A61J 7/00* (2006.01)
*A61M 39/28* (2006.01)

(52) U.S. Cl.
CPC ............ *A61J 7/0053* (2013.01); *A61M 39/28* (2013.01); *A61M 2202/0466* (2013.01); *A61M 2205/502* (2013.01); *A61M 2205/505* (2013.01); *A61M 2210/0625* (2013.01)

(58) Field of Classification Search
CPC .......... A61J 7/0053; A61J 9/00; A61M 39/28; A61M 2202/0466; A61M 2205/502; A61M 2205/505; A61M 2210/0625; A61M 16/0683; A61C 17/0211; A61C 17/00; A61C 17/02; A61B 10/0051; A61B 10/0045; A61B 10/00
See application file for complete search history.

(56) References Cited

U.S. PATENT DOCUMENTS

| 2,756,740 | A | * | 7/1956 | Deane | A61J 15/0011 |
| | | | | | 604/77 |
| 2,969,064 | A | * | 1/1961 | Metz | A61M 39/284 |
| | | | | | 604/77 |
| 4,463,859 | A | * | 8/1984 | Greene | A61J 9/00 |
| | | | | | 215/11.1 |
| 4,578,055 | A | * | 3/1986 | Fischer | A61M 3/022 |
| | | | | | 604/2 |
| 4,796,628 | A | * | 1/1989 | Anderson | A61J 15/0011 |
| | | | | | 606/236 |
| 4,813,933 | A | * | 3/1989 | Turner | A61J 15/0011 |
| | | | | | 604/79 |
| 4,950,254 | A | * | 8/1990 | Andersen | A61J 15/0026 |
| | | | | | 604/213 |
| 5,057,077 | A | * | 10/1991 | Turner | A61J 15/0011 |
| | | | | | 604/247 |

(Continued)

FOREIGN PATENT DOCUMENTS

| GB | 2202449 A | * | 9/1988 | ................ A61J 9/00 |
| GB | 2220363 A | * | 1/1990 | .......... A61J 15/0053 |

*Primary Examiner* — Nathan R Price
*Assistant Examiner* — Mark A Igel
(74) *Attorney, Agent, or Firm* — Oltman, Flynn & Kubler; Frank L. Kubler

(57) ABSTRACT

An apparatus for delivering a metered stream of saliva solution includes a delivery tube for drawing a saliva solution from a solution source; a pumping and metering device connected to the delivery tube for pumping saliva solution from the solution source through the delivery tube and delivering the solution to a user mouth, the delivery tube having a delivery tube upstream segment for extending from the solution source to the device, and a delivery tube downstream segment extending from the device to a delivery tube free end for placement in a user mouth; and a mouthpiece mounted to the delivery tube free end for engaging and securely retaining the delivery tube free end within a user mouth until released.

11 Claims, 15 Drawing Sheets

(56) References Cited

U.S. PATENT DOCUMENTS

| | | | | |
|---|---|---|---|---|
| 5,181,910 | A * | 1/1993 | Scanlon | A61M 5/172 128/DIG. 12 |
| 5,217,468 | A * | 6/1993 | Clement | A61B 10/02 606/114 |
| 5,484,405 | A * | 1/1996 | Edstrom, Sr. | A61J 15/0011 604/77 |
| 5,911,406 | A * | 6/1999 | Winefordner | A45F 3/16 251/339 |
| 6,199,729 | B1 * | 3/2001 | Drzymkowski | A45F 3/20 138/120 |
| 7,320,678 | B2 * | 1/2008 | Ruth | A61J 9/00 604/77 |
| 10,646,676 | B1 * | 5/2020 | Matich | A61M 16/0666 |
| 2007/0204867 | A1 * | 9/2007 | Kennedy, Jr. | A61C 17/0211 128/859 |
| 2008/0077073 | A1 * | 3/2008 | Keenan | A61M 5/142 604/19 |
| 2009/0123886 | A1 * | 5/2009 | Vaska | A61F 5/566 433/27 |
| 2011/0027746 | A1 * | 2/2011 | McDonough | A61C 17/0211 433/80 |
| 2011/0265801 | A1 * | 11/2011 | Cullen | A61F 5/56 128/848 |
| 2013/0042876 | A1 * | 2/2013 | Hermanson | A61M 15/00 128/848 |
| 2013/0319079 | A1 * | 12/2013 | Simons | A61B 5/4011 73/23.34 |
| 2015/0128941 | A1 * | 5/2015 | Holley | A61M 16/1055 128/203.14 |
| 2017/0056144 | A1 * | 3/2017 | Levy | A63B 71/081 |
| 2018/0360692 | A1 * | 12/2018 | Sieffert | A61H 21/00 |
| 2019/0183619 | A1 * | 6/2019 | Reizenson | A61C 1/0084 |
| 2020/0188622 | A1 * | 6/2020 | Borvan | A61M 16/0495 |

* cited by examiner

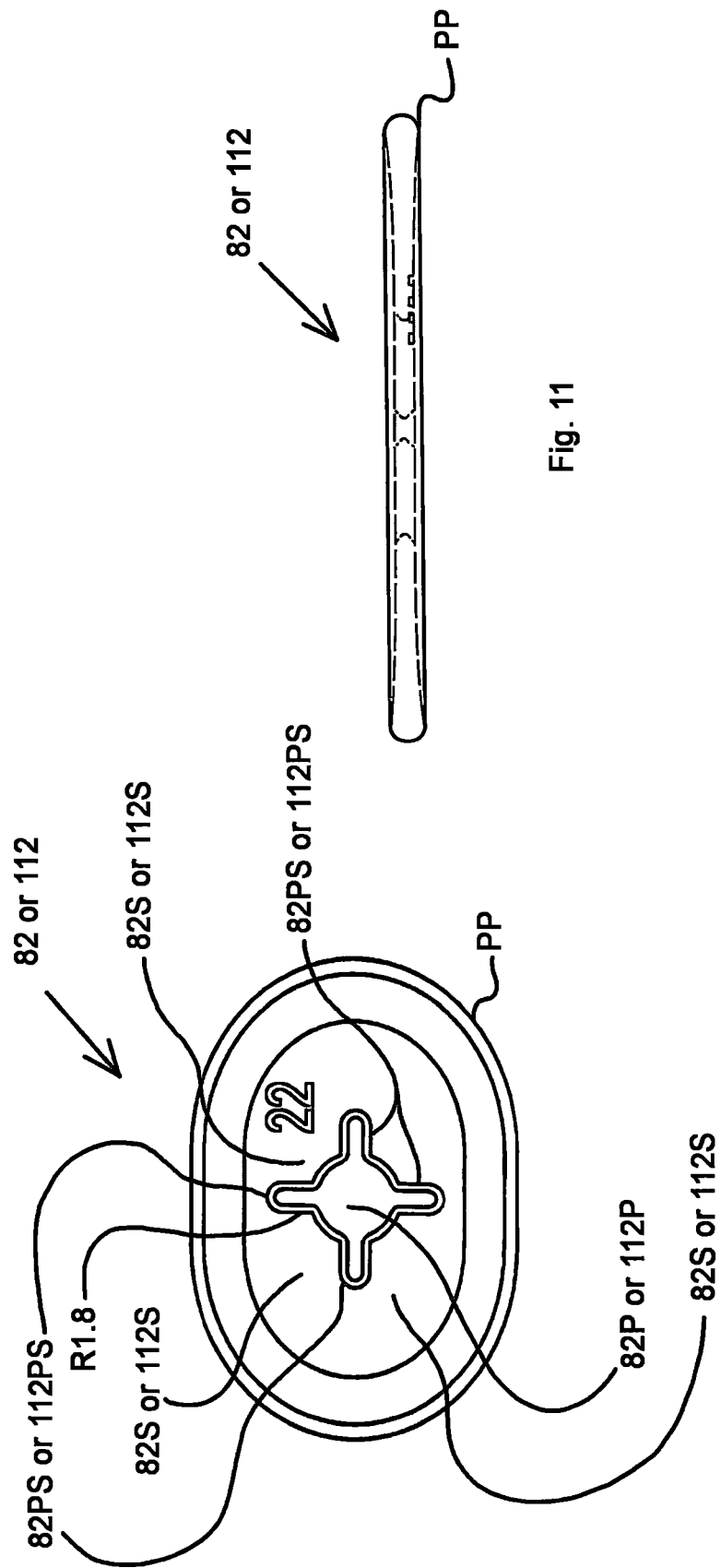

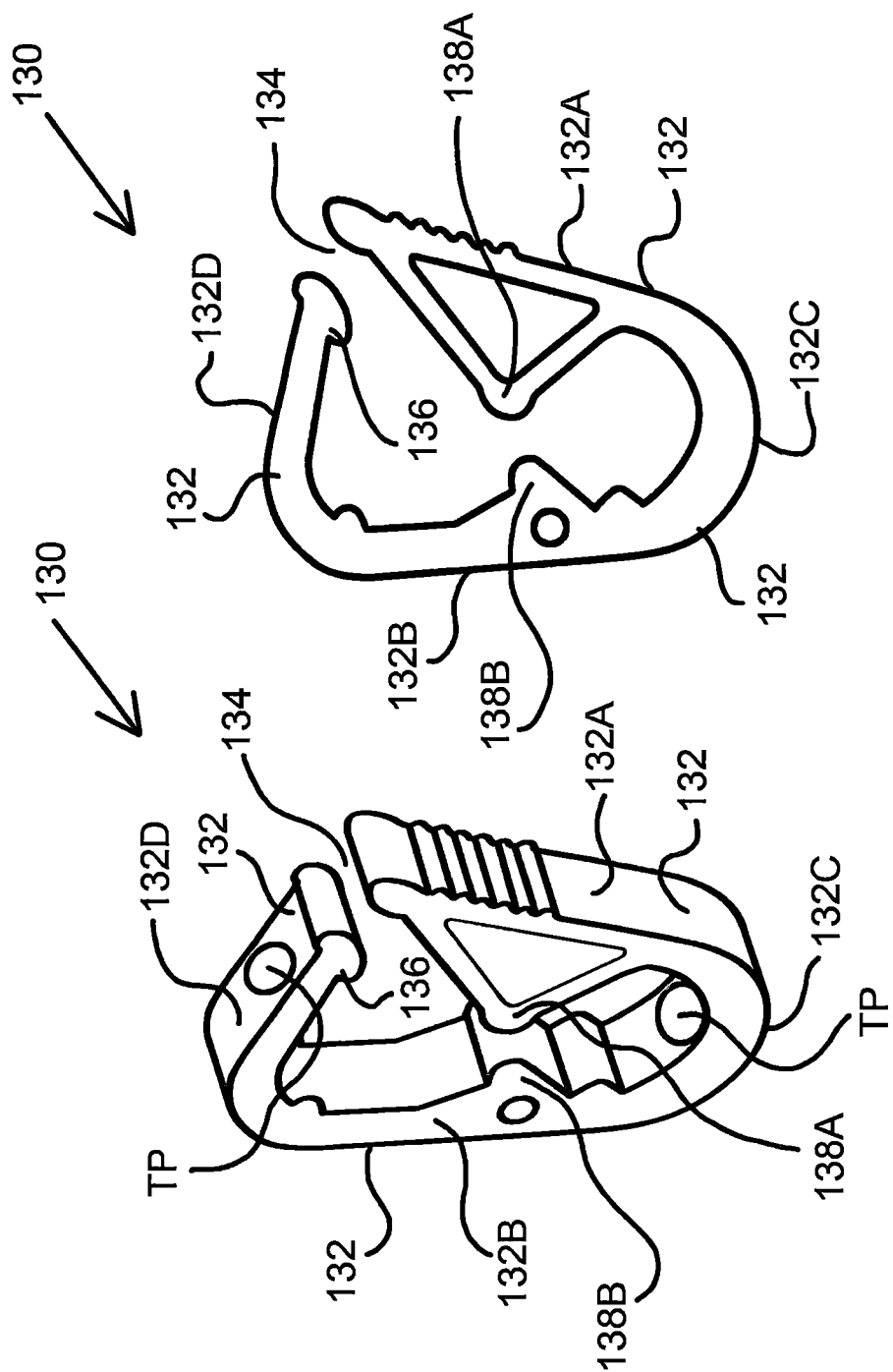

US 11,877,984 B1

SALIVA SOLUTION METERING APPARATUS WITH DELIVERY TUBE RETAINING MOUTHPIECE

BACKGROUND OF THE INVENTION

1. Field of the Invention

The present invention relates to an apparatus for delivering and metering the flow of a liquid in the form of a saliva solution such as substitute saliva into the mouth of a user through a delivery tube having a delivery tube free end, which is securely retained within a user mouth by a retaining mouthpiece.

The delivery tube draws saliva solution from a solution source, such as a source bag, a pumping and metering mechanism, preferably in the form of a device engaging the delivery tube, to pump the solution from the source through the delivery tube and deliver the pumped solution into a user mouth. The delivery tube has a delivery tube upstream segment extending from the source to the device, and a delivery tube downstream segment extending from the device to the delivery tube free end, and the inventive mouthpiece mounted on the delivery tube free end, permitting the user to comfortably engage and securely retain within his or her mouth the delivery tube free end until released by the user opening his or her mouth. The solution source preferably is elevated relative to the pumping and metering device to gravity feed solution to the device. A shut-off valve optionally is provided between the device and the delivery tube free end, in the form of a clip resiliently gripping the tube to stop and start the flow of solution.

The pumping and metering device delivers the solution at a selected flow rate sufficient to prevent oral dehydration due to any of various medical conditions. The device continues to pump at the selected rate until a pre-set maximum volume is reached, and then stops.

The mouthpiece includes a tube retaining washer in the form of a mouthpiece panel having a central panel port, the delivery tube free end passing through the panel port and extending beyond the panel to extend into a user mouth. The delivery tube is releasably retained within the panel port by a tube engaging mechanism. The delivery tube free end is inserted into the user mouth and between upper and lower sets of user teeth, with the retaining panel extending radially outward from the tube between the forward faces of the user teeth and the user lips, so that the panel and the tube free end are held in place to deliver saliva solution as long as the user mouth remains closed. The mouth piece preferably includes a second panel, mounted around the tube in the same way that the first panel is mounted and, like first panel, has a second panel port through which tube is fitted. Second panel port preferably has a tube engaging mechanism like that of first panel port, and thus preferably takes the form of radial slits extending outwardly from second panel port, to define resilient panel sections which resiliently bear against and grip tube. Second panel is spaced from first panel in a direction away from the tube free end, as illustrated, preferably by one-eighth to one quarter of an inch, so that user teeth can fit closely between first and second panels. Upon insertion of the mouthpiece, and closing of the user mouth, the first panel is positioned adjacent to the user teeth forward faces and the second panel is positioned adjacent to the user teeth rearward faces, so that the two panels retain the tube against substantial forward or rearward movement relative to user teeth. The tube free end and mouthpiece are released simply by the user opening his or her mouth and lifting them out. The panel perimeter preferably is elliptical. The diameter of the central panel port through which the delivery tube free end passes preferably matches or is slightly smaller than the delivery tube outer diameter, so that friction between the delivery tube and the panel port edges functions as the tube engaging mechanism, holding the panel on the tube.

2. Description of the Prior Art

As a result of certain medical conditions, there has long been a need for a device for delivering saliva solution into a person's mouth for proper hydration.

It is thus an object of the present invention to provide a saliva solution delivering and metering apparatus for delivering a saliva solution into a user mouth at a selected rate and optionally up to a selected maximum volume.

It is another object of the present invention to provide such an apparatus having a delivery tube with a delivery tube free end, and having a mouthpiece capable of retaining the delivery tube free end in the mouth of a user comfortably and securely.

It is still another object of the present invention to provide such an apparatus in which the mouthpiece is easily removable from the user mouth, simply by opening the user mouth and lifting it out.

It is yet another object of the present invention to provide such a saliva solution delivering and metering apparatus which includes clamps for mounting elements of the apparatus to a stand such as an IV stand so that a source bag containing saliva solution is elevated above the metering device and the delivery tube is mounted to the outward end of an arm or prong protruding over the head of a user bed, so that the delivery tube can extend downwardly to the use It is finally an object of the present invention to provide such an apparatus which is compact, easy to use, reliable and relatively inexpensive.

SUMMARY OF THE INVENTION

The present invention accomplishes the above-stated objectives, as well as others, as may be determined by a fair reading and interpretation of the entire specification.

An apparatus is provided for delivering a metered stream of saliva solution, the apparatus including a delivery tube for drawing a saliva solution from a solution source; a pumping and metering device connected to the delivery tube for pumping saliva solution from the solution source through the delivery tube and delivering the solution to a user mouth, the delivery tube having a delivery tube upstream segment for extending from the solution source to the device, and a delivery tube downstream segment extending from the device to a delivery tube free end for placement in a user mouth, and a mouthpiece mounted to the delivery tube free end for engaging and securely retaining the delivery tube free end within a user mouth until released.

The solution source preferably is a source bag. The mouthpiece preferably includes a panel having a panel port, where the delivery tube free end passes through the panel port and extends beyond the panel, to extend into a user mouth, where the delivery tube free end is releasably retained within the panel port by a tube engaging mechanism; so that the delivery tube free end can be placed within a user mouth and between upper and lower sets of user teeth, so that the retaining panel extends radially outward from the tube between forward faces of user teeth and user lips, thereby holding the panel and the delivery tube free end in the user mouth while the user mouth is closed, to deliver saliva solution into the user mouth.

The apparatus panel perimeter preferably is substantially elliptical and sized so that when placed in a user mouth the ellipse short diameter extends generally parallel to the length of individual user teeth and terminates at panel upper and lower ends short of making uncomfortable contact with user gums, while the ellipse long diameter extends laterally across user teeth forward faces for maximized panel abutment.

The diameter of the panel port through which the delivery tube free end passes preferably substantially matches or is smaller than the outer diameter of the delivery tube, so that friction between the delivery tube and edges of the panel port functions as the tube engaging mechanism, releasably holding the panel on the tube. The device comprises a pump for pumping the solution through the delivery tube, a keypad for entering desired flow rate selection data into the device, and a display for showing selected flow rate data.

BRIEF DESCRIPTION OF THE DRAWINGS

Various other objects, advantages, and features of the invention will become apparent to those skilled in the art from the following discussion taken in conjunction with the following drawings, in which:

FIG. 10 is a close-up, front, plan view of either of the first and second mouthpiece panels.

FIG. 11 is an edge view of the panel of FIG. 10, with the concave inner contour shown in broken lines.

FIG. 13 is a perspective view of the preferred shut-off clamp.

FIG. 14 is a plan, side view of the shut-off clamp of FIG. 13.

DETAILED DESCRIPTION OF THE PREFERRED EMBODIMENTS

Figure 1:
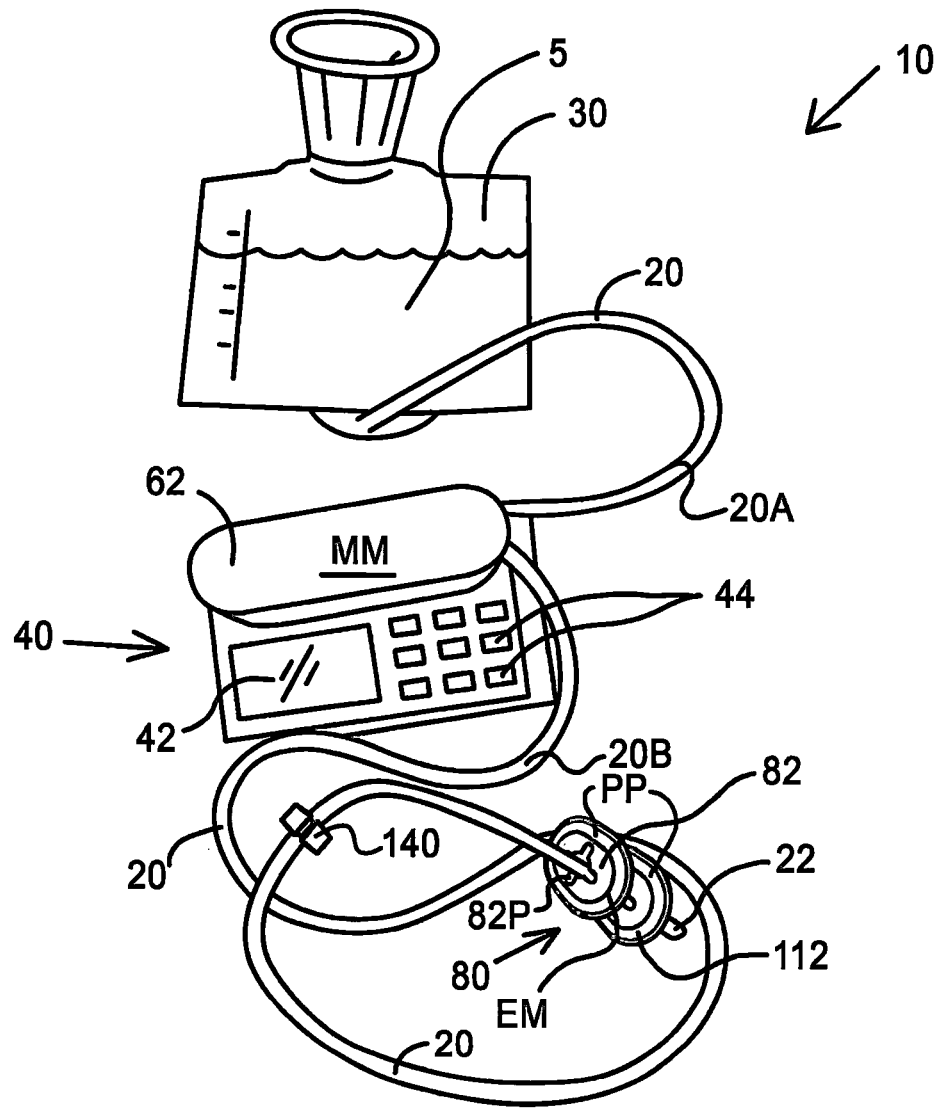
FIG. 1 is a top view of the present apparatus and solution source resting on a horizontal support surface, this version of the apparatus including the preferred INFINITY™ pumping and metering device manufactured by MOOG™ and a resilient clip shut-off valve.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

PREFERRED EMBODIMENTS

Referring to FIGS. 1-19, an apparatus 10 is disclosed for delivering and metering the flow of a liquid in the form of a saliva solution or substitute saliva (hereinafter collectively saliva solution S into the mouth of a user through a delivery tube.

Figure 2:
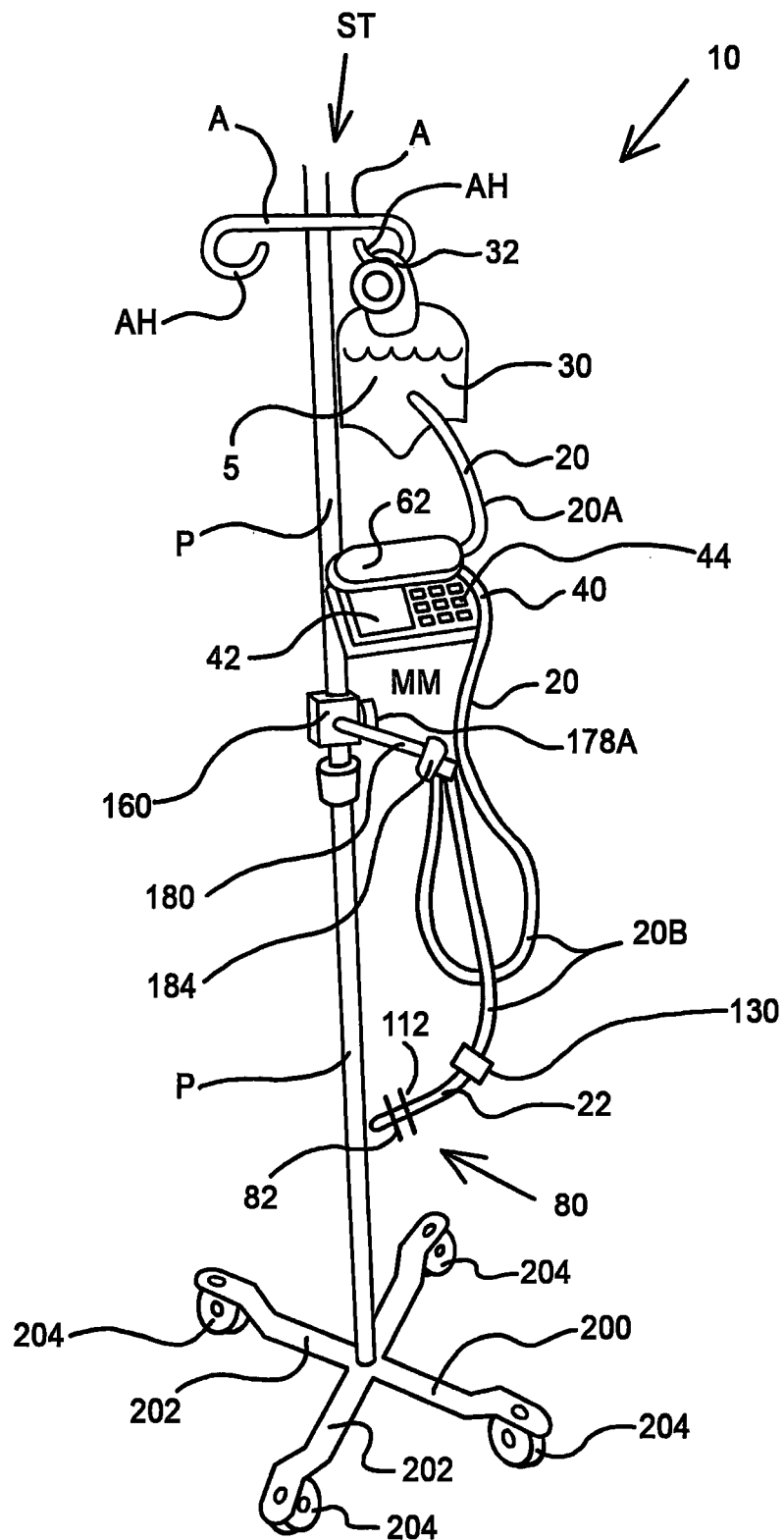
FIG. 2 is a perspective front view of the present invention mounted to a rolling IV (intravenous fluid bag mounting) stand, including a prong projecting forwardly from the stand to which the delivery tube is releasably secured with a tie strap.
Figure 3:
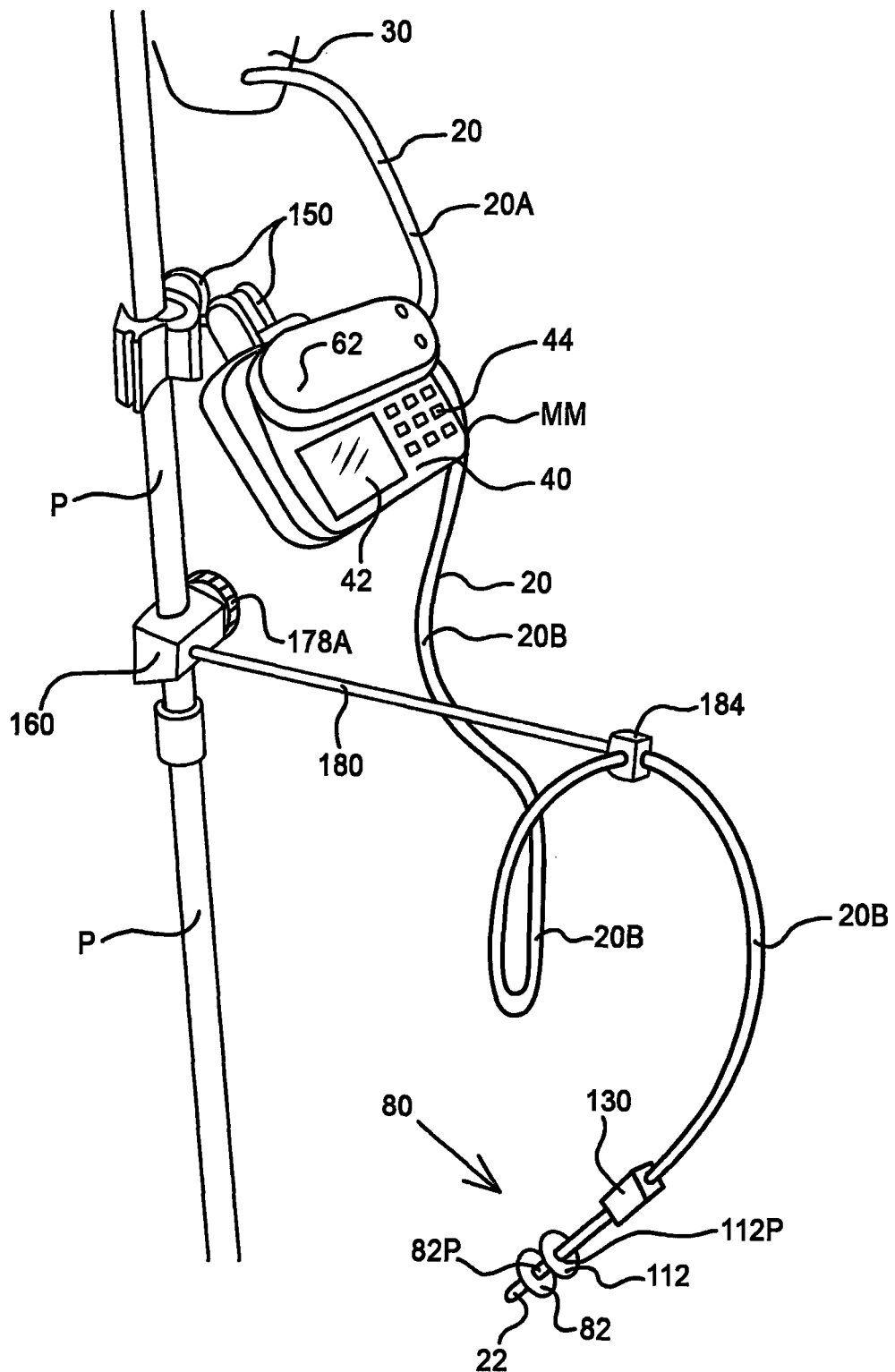
FIG. 3 is a broken away side perspective view as in FIG. 2, revealing the pole clamp mounting the metering device to the pole portion of the IV stand.
Figure 4:
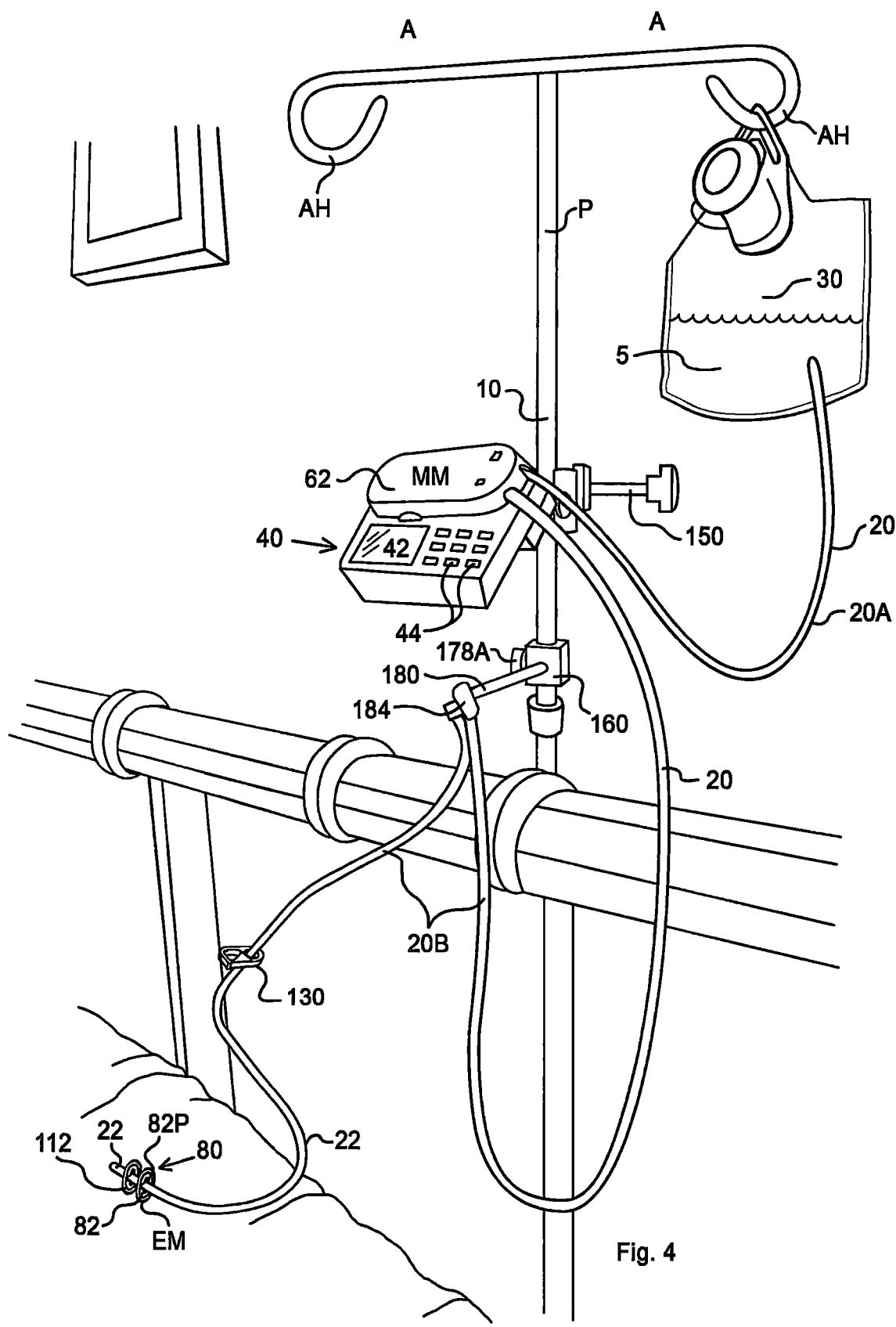
FIG. 4 is a perspective view of the present apparatus mounted to an IV stand a pole with the delivery tube extending downwardly to reach a user mouth, which is a preferred arrangement to prevent a user from becoming tangled in the delivery tube.
Figure 5:
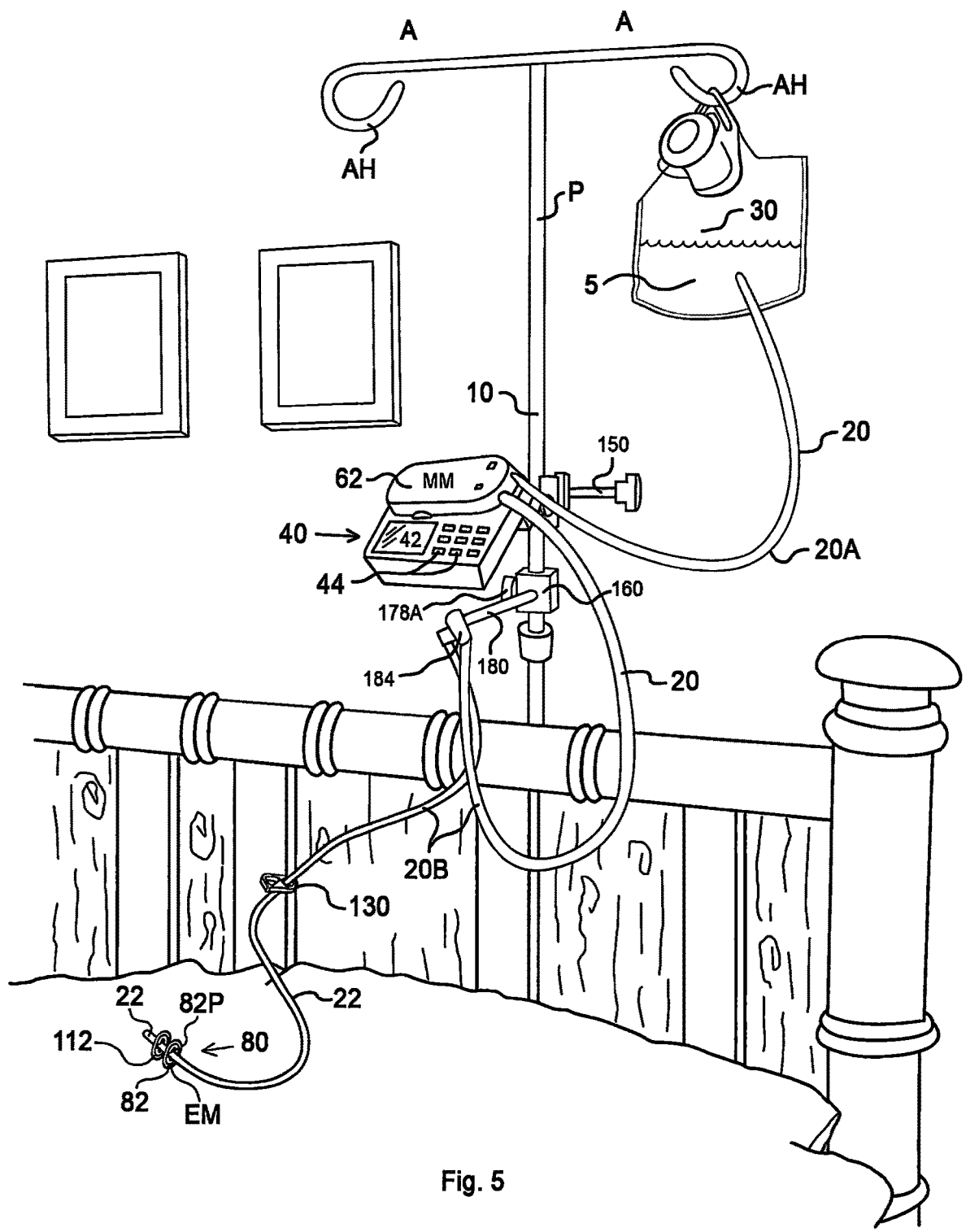
FIG. 5 shows the apparatus mounted to an IV stand as in FIG. 2, where the stand is once again positioned behind a headboard for user access while in bed.
Figure 6:
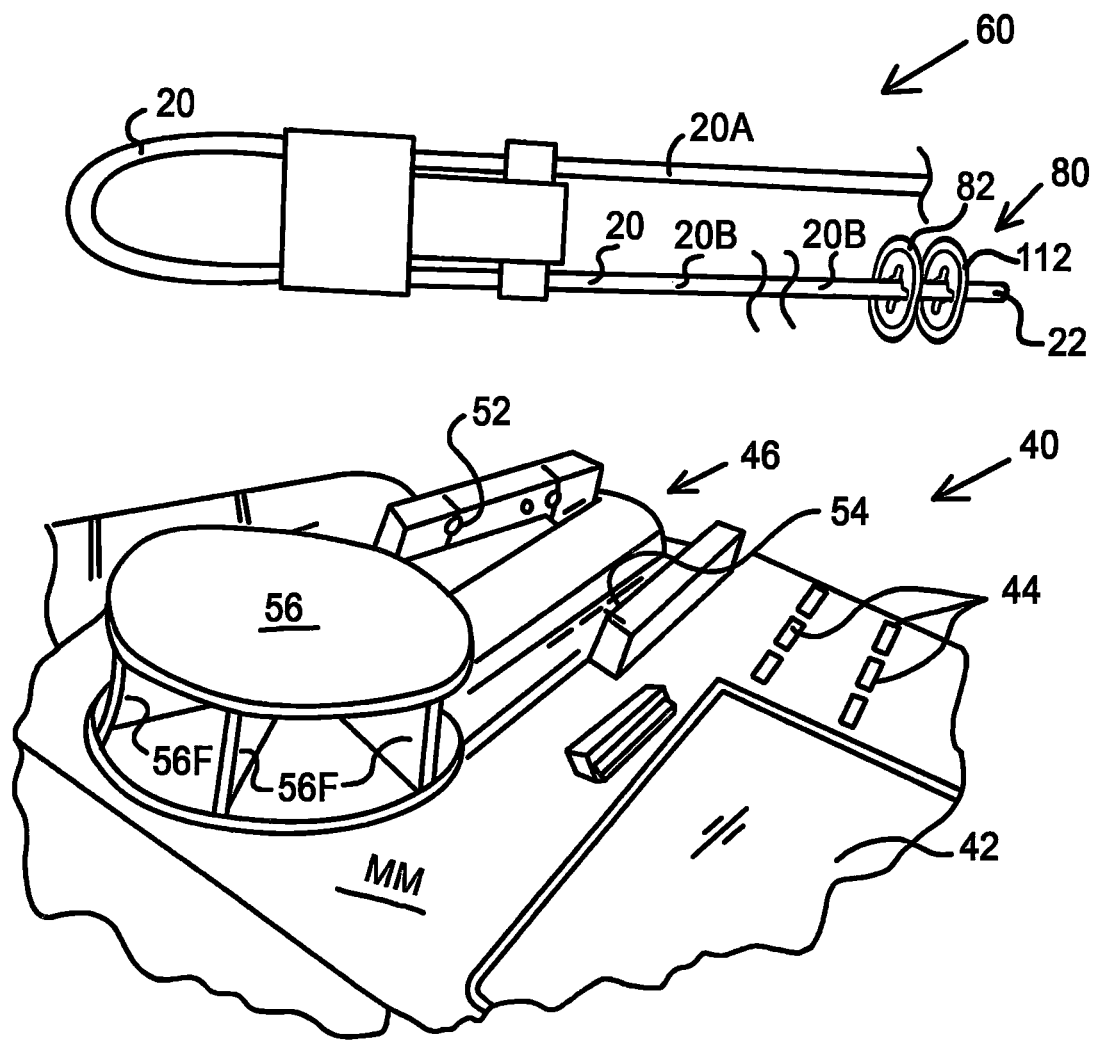
FIG. 6 is a view of the apparatus including a broken away perspective view of the INFINITY™ device tube cassette receptacle, pump wheel, keypad and display, with the tube cassette and connected mouthpiece shown removed and separate from the device.
Figure 7:
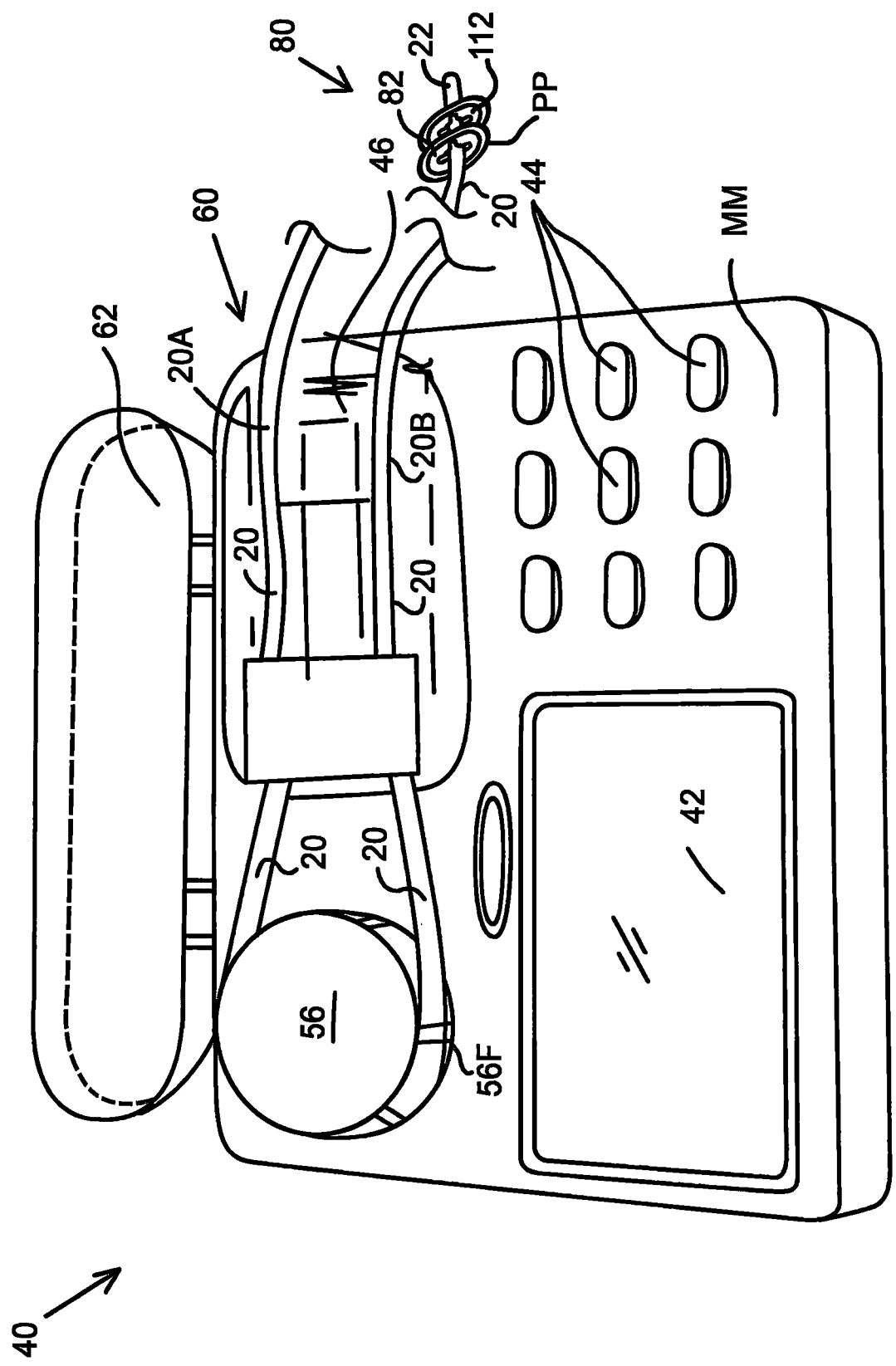
FIG. 7 is a top perspective view of the preferred INFINITY™ device with the cassette door open to reveal the mounted tube cassette and the present mouthpiece.
Figure 8:
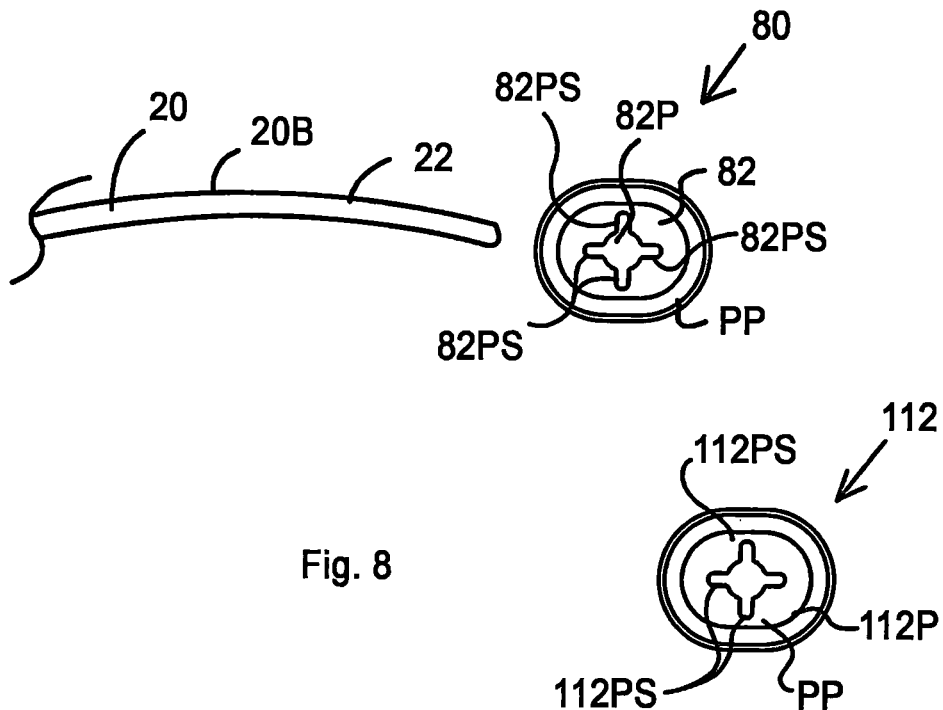
FIG. 8 is a disassembled view of the mouthpiece, including a broken away view of the delivery tube free end, and plan views of the first and second mouthpiece panels placed next to the tube free end, showing the preferred mouthpiece panel elliptical shape.

The apparatus 10 includes a delivery tube 20 that draws saliva solution S from a solution source 30 such as a source bag 30, a pumping and metering mechanism MM, preferably in the form of a device 40 engaging the delivery tube 20 to pump the solution from the source 30 through the delivery tube 20 and deliver the pumped solution S into a user mouth. The delivery tube 20 has a delivery tube upstream segment 20A extending from the source 30 to the device 40, and a delivery tube downstream segment 20B extending from the device 40 to the delivery tube free end 22, and an inventive mouthpiece 80 mounted on the delivery tube free end 22, permitting the user to comfortably engage and securely retain within his or her mouth the delivery tube free end 22 until released by the user opening his or her mouth. The solution source 30 preferably is elevated relative to the device 40 for gravity feeding of solution S to the device 40. A shut-off valve 130 preferably is provided between the device 40 and the delivery tube free end 22, in the form of a clip resiliently gripping the tube 20. As shown in FIG. 1, the shut-off valve 130 closes solution flow when gripping the tube 20 and opens solution flow when removed from tube 20. FIG. 2 shows a perspective view of the metering mechanism MM mounted to an upright pole P which is part of a stand ST. Stand ST preferably an intravenous fluid stand or IV stand, as illustrated.

Shut-off clamp 130 preferably includes an elongate looped strip 132 of resilient material having a first long side 132A and a second long side 132B, and a first short side 132C and a second short side 132D. See FIGS. 12-14. There is a break 134 in the strip 132 between the second short side 132D and the first long side 132A, and the second short side 132D has an engaging notch 136 into the first long side free end 132AF can releasably but engagingly fit, to hold the looped strip 132 in a contracted position, in which first and second long sides 132A and 132B are pivoted toward each other. First and second short sides 132C and 132D have tube passing ports TP, so that the tube 20 can pass through the shut-off clamp 130 between the first and second longs sides 132A and 132B. The first and second long sides 132A and 132B have inwardly protruding first and second closure bulges 138A and 138B, respectively, which bear firmly against the tube 20 when the first long side free end 132AF is fitted into the engaging notch 136, to fully close the tube 20 against the passage of solution S as long as the first long side free end 132AF remains engaged in engaging notch 136. To open clamp 130 to again permit solution S passage, first long side free end 132AF is released from engaging notch 136, so that the resilience of the clamp 130 material as well as the resilience of the tube 20 cause the first and second long sides 132A and 132B to pivot away from each other, so that the closure bulges 138A and 138B separate and no longer compress tube 20.

The pumping and metering device 40 delivers the solution S at a flow rate sufficient to prevent oral dehydration due to any of various medical conditions such as, for example, a flow rate of 4.0 to 7.3 milliliters per hour. The flow rate is important, in part, because a rate that is too fast could result in the user aspiration. The device 40 continues to pump at the selected flow rate until a pre-set maximum volume is reached, and then stops. Different saliva solutions S are believed to require different optimum delivery flow rates.

Figure 9:
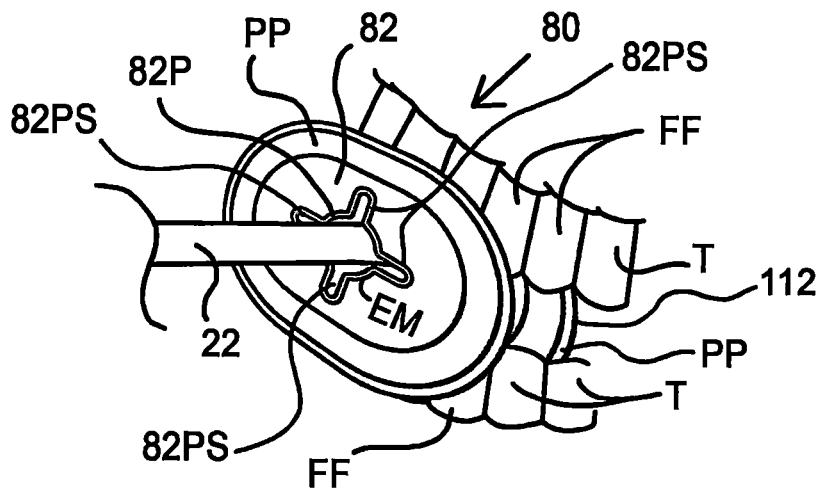
FIG. 9 is an assembled view of the mouthpiece in use, including a perspective view of the delivery tube free end fitted between user teeth and the mouthpiece panels adjacent to or resting against the forward and rearward faces of the user teeth.
Figure 12:
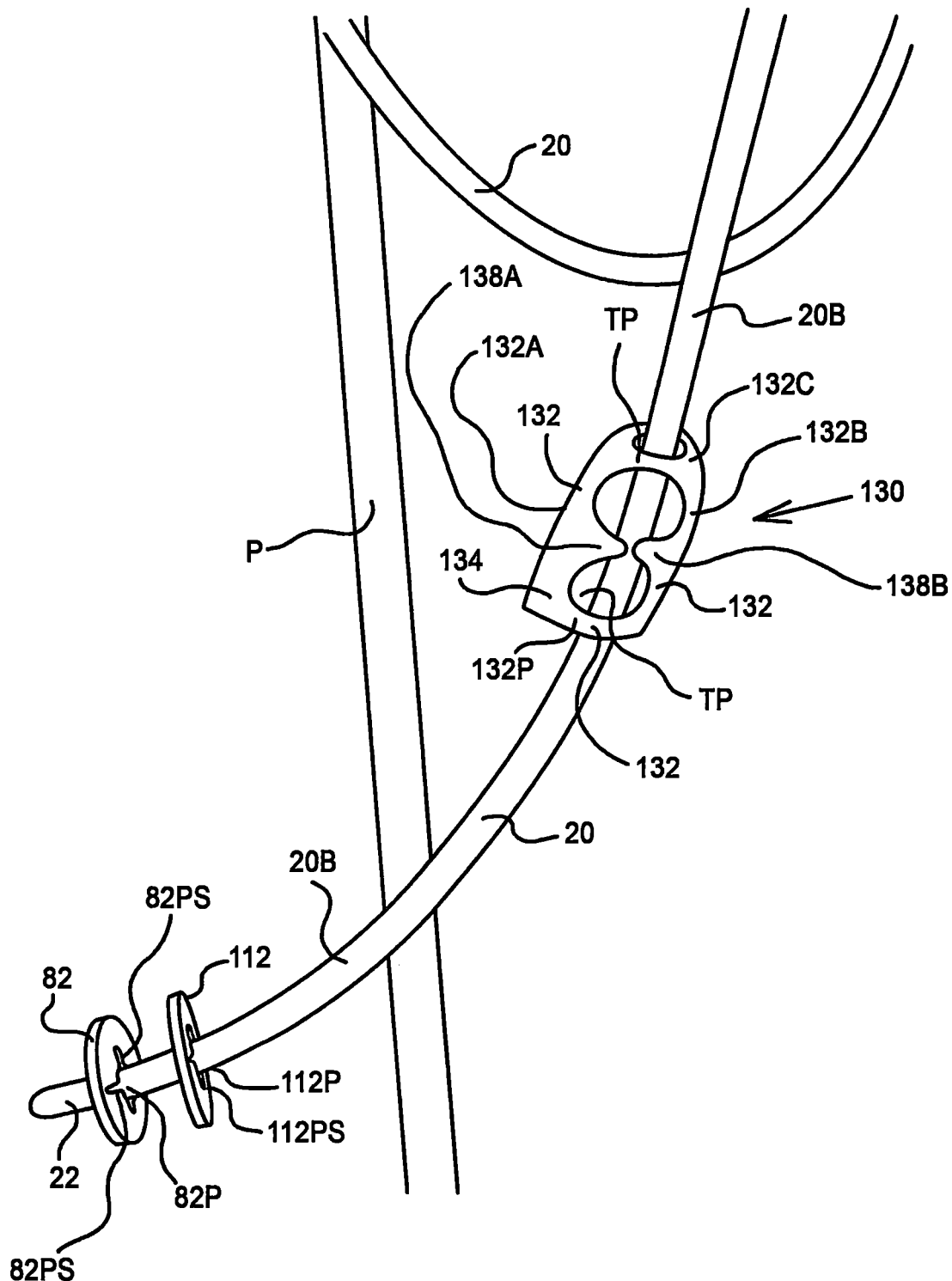
FIG. 12 is a broken away, perspective view of the apparatus mounted on the stand as in FIG. 7 showing close-up views of the shut-off clamp and the first and second panels of the mouthpiece.
Figure 15:
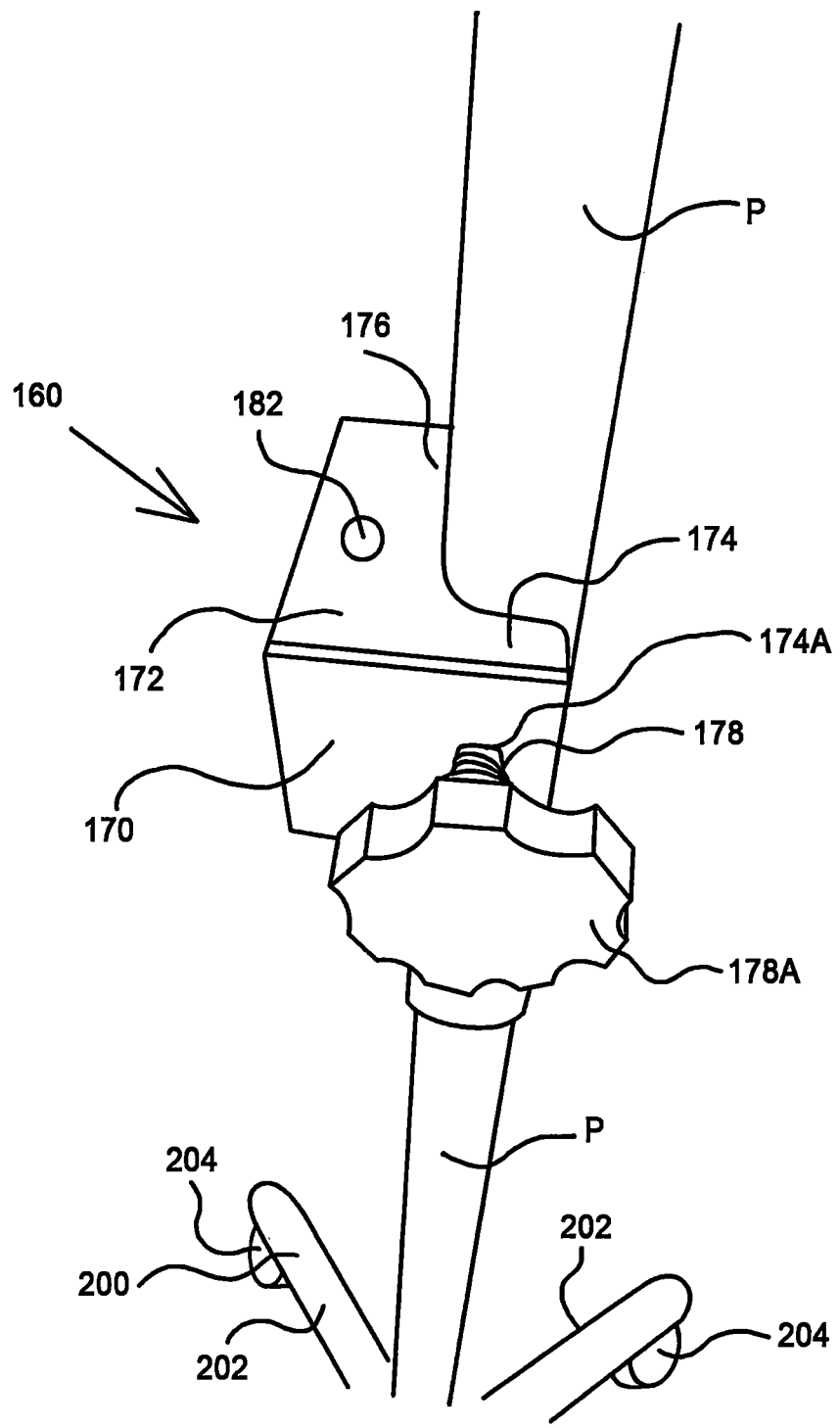
FIG. 15 is a broken-away, perspective view of the stand and a close-up view of the anchor prong clamp and its screw dial, with the prong removed.
Figure 17:
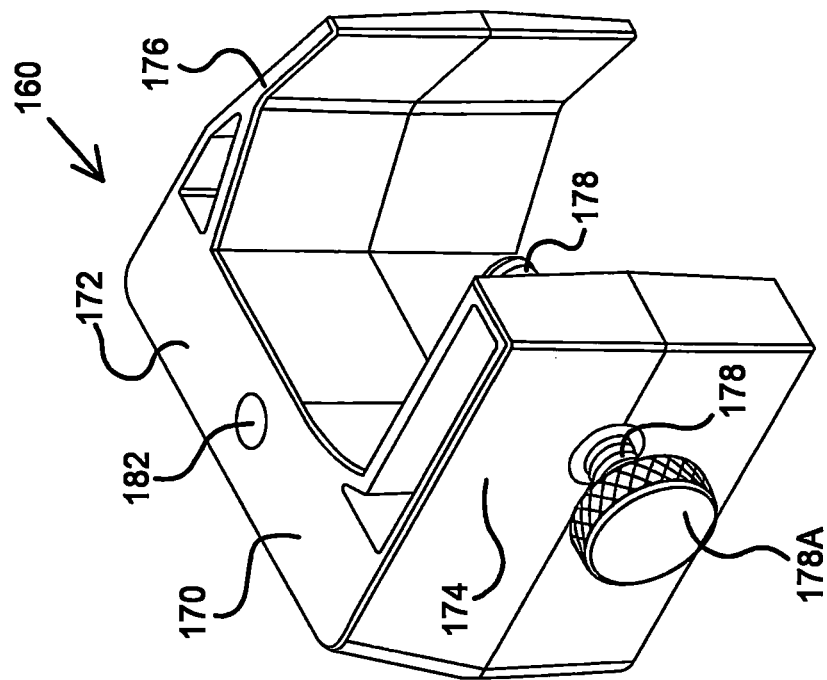
FIG. 17 is a frontward perspective view of the prong clamp of FIG. 16.
Figure 16:
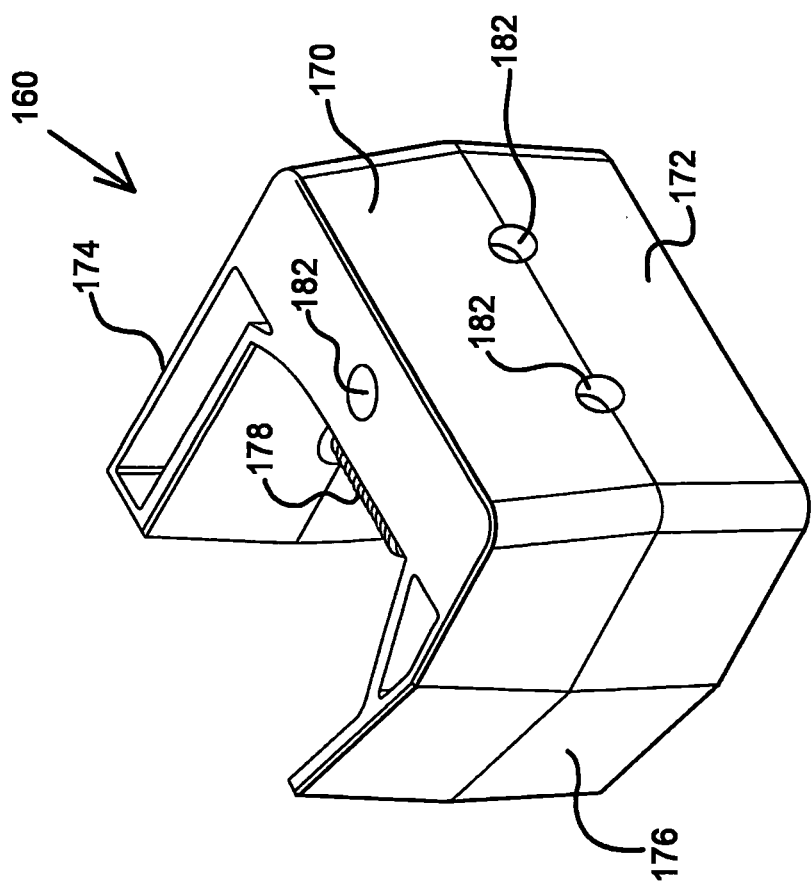
FIG. 16 is a rearward, perspective, separate view of the anchor prong clamp of FIG. 15.
Figure 18:
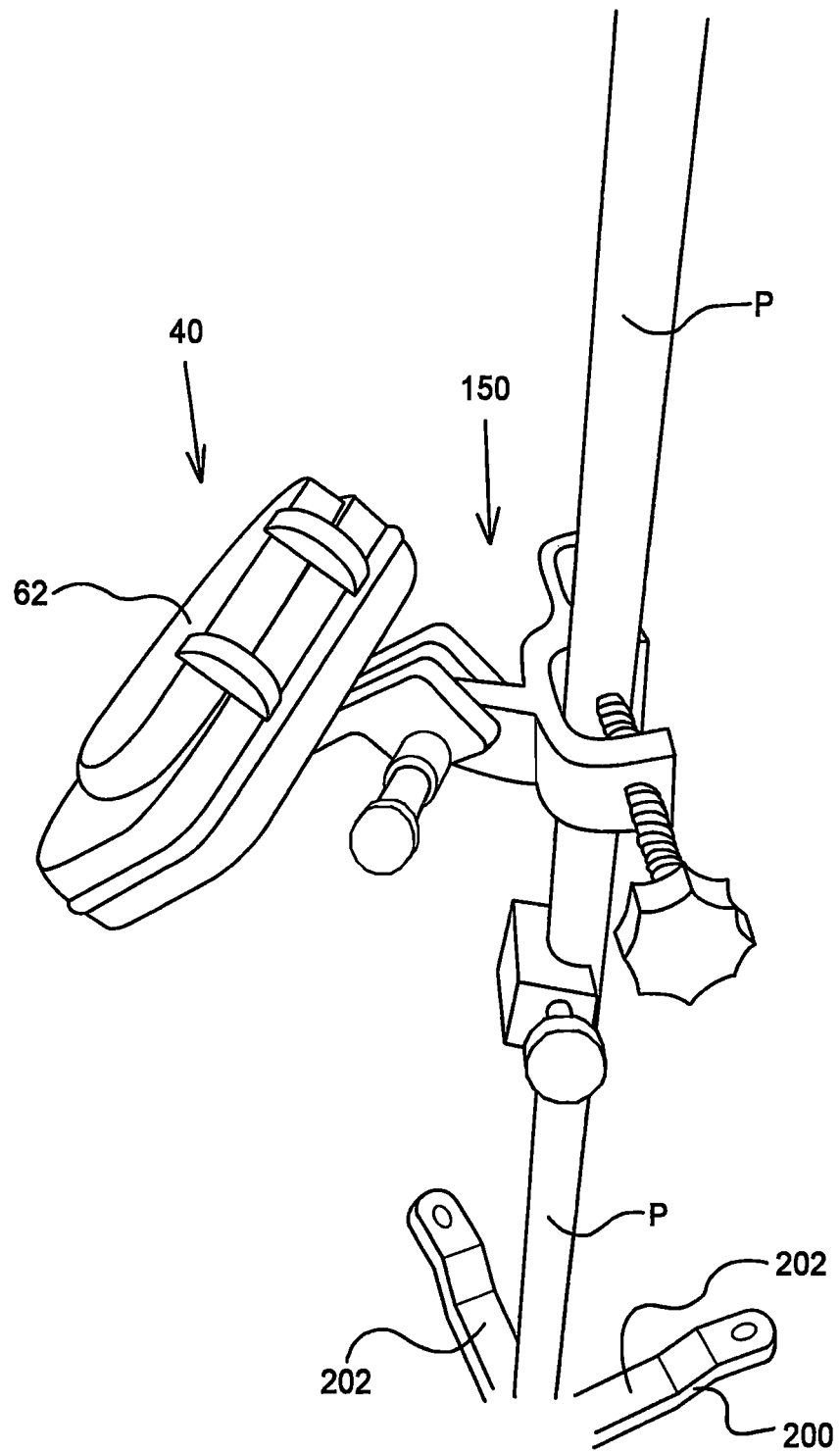
FIG. 18 is a broken-away, perspective view of the stand, and a close-up view of the metering device pole clamp and its central pivot connection, the pole clamp connecting the metering device to the stand.
Figure 19:
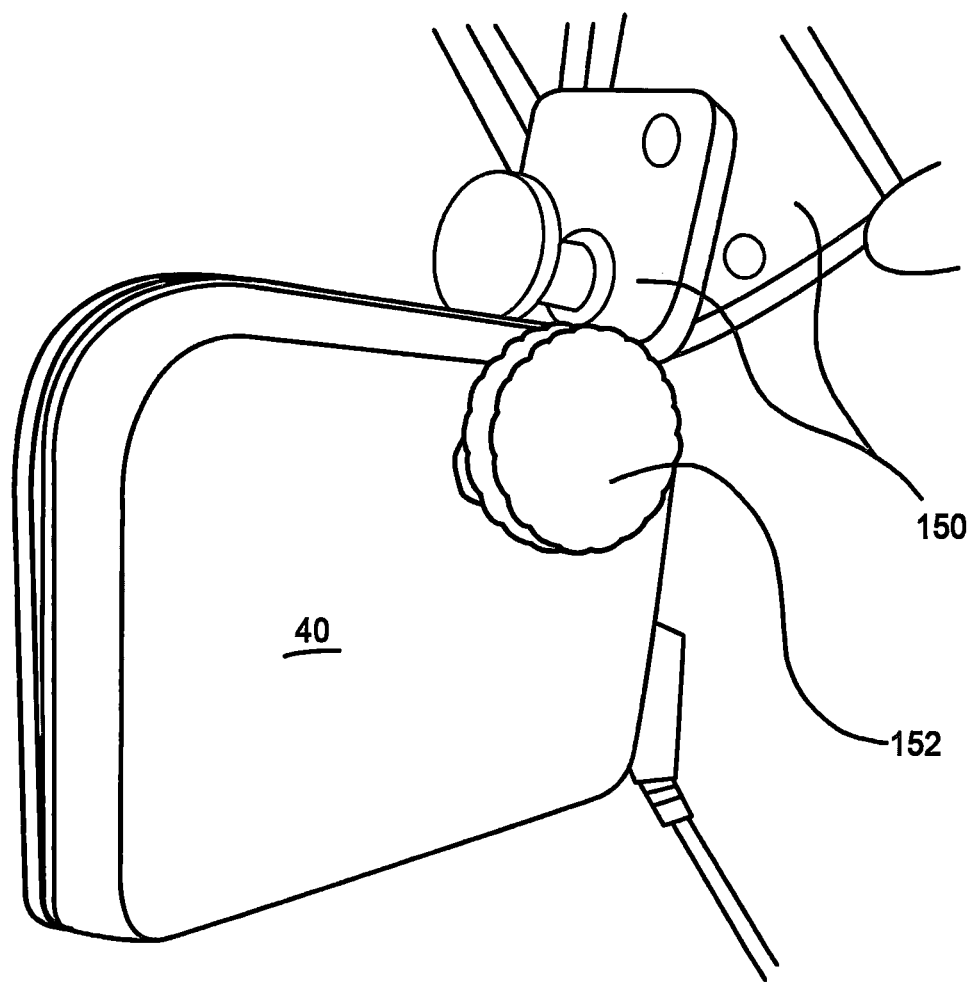
FIG. 19 is a perspective view of the metering device and its pole clamp of FIG. 18.

The mouthpiece 80 includes a tube retaining washer in the form of a mouthpiece first panel 82 having a first panel port 82P preferably located at the center of first panel 82, the delivery tube free end 22 passing through the first panel port 82P and extending beyond the panel 82 to extend into a user mouth. See FIGS. 1-8 and 10. First panel port 82P preferably has a diameter smaller than that of delivery tube 20, and tube 20 is releasably retained within the panel port 82P by a tube engaging mechanism EM. Tube engaging mechanism EM preferably takes the form of radial slits 82PS extending outwardly from first panel port 82P, to define resilient panel sections 82S which resiliently bear against and grip tube 20. As shown in FIG. 9, the delivery tube free end 22 is inserted into the user mouth and between upper and lower sets of user teeth T, with the retaining first panel 82 extending radially outward from the tube 20 between the forward faces FF of the user teeth T and the user lips, so that the panel 82 and the delivery tube free end 22 are held in place to deliver saliva solution S as long as the user's mouth remains closed. The mouth piece 80 preferably includes a second panel 112, mounted around the tube 20 in the same way that the first panel 82 is mounted and, like first panel 82, has a second panel port 112P through which tube 20 is fitted. Second panel port 112P preferably has a tube engaging mechanism EM like that of first panel port 82P, and thus preferably takes the form of radial slits 112PS extending outwardly from second panel port 112P, to define resilient panel sections 112S which resiliently bear against and grip tube 20. See FIGS. 8-11. Second panel 112 is spaced from first panel 82 in a direction away from the tube free end 22, as illustrated, preferably by one-eighth to one quarter of an inch, so that user teeth T can fit closely between first and second panels 82 and 112. Upon insertion of the mouthpiece 80, and closing of the user mouth, the first panel 82 is positioned adjacent to the user teeth forward faces FF and the second panel 112 is positioned adjacent to the user teeth rearward faces RF, so that the two panels 82 and 112 retain the tube 20 against substantial forward or rearward movement relative to user teeth T. See FIG. 9. First and second panels 82 and 112 may be the same size or of different sizes, where the second panel 112 is optionally the smaller of the two, to fit more comfortably behind the user teeth T. Example panel 82 and panel 112 dimensions, which are understood to be in no way limiting, are \_\_\_\_\_×\_\_\_\_\_ inches, and \_\_\_\_\_×\_\_\_\_\_ inches, respectively. The tube free end 22 and mouthpiece 80 are released simply by the user opening his or her mouth and lifting them out. The panel perimeters PP preferably are elliptical, and are placed in the user mouth so that the short diameter or minor axis extends parallel to individual user teeth and terminates at panel 82 or 112 upper and lower ends, short of making uncomfortable contact with user gums. The long diameter or major axis extends laterally across the tooth forward faces FF or tooth rearward faces RF. This arrangement provides maximized panel 82 abutment area, so that the delivery tube free end 22 is retained securely and stably. The diameter of the panel port 82P, through which the delivery tube free end 22 passes preferably, as noted above, matches or is slightly smaller than the delivery tube 20 outer diameter, so that friction between the delivery tube 20 and the panel port 82P edges functions as the tube engaging mechanism EM, holding the panel 82 on the tube 20.

The source bag 30 is filled with saliva solution or solution S and thus becomes the present solution source 30. See FIGS. 1, 2, 4 and 5. The device 40 is primed to the delivery tube free end 22, and the flow rate and maximum volume of solution S to be delivered are input into the keypad 44 using existing INFINITY™ programming. The maximum volume alternatively can be reached simply when the source 30 runs out of solution. The delivery tube free end 22 should be retained on the high side of the user mouth when the user is lying down. This can be controlled with the user tongue. The device 40 has to be primed, before it can operate properly.

Metering device 40 preferably is releasably secured to pole P at a selected elevation by an inventive metering device pole clamp 150, such as ZEVEX Enteral Lite Adjustable Pole Clamp 29158-001 Rev. B. See FIGS. 3, 18 and 19. This is the pole clamp 150 illustrated in the drawings. A device mounting bolt fitted with a hand grip mounting bolt dial 152 screws through a threaded bore in pole clamp 150 and into a threaded hole in the back of metering device 40 to removably mount device 40.

An example of a preferred pumping and metering device 40 is the MOOG™ INFINITY™ ORANGE liquid food delivery device, designed to deliver formula or human milk to an infant. See FIGS. 4-7. The INFINITY™ includes a digital display 42 and a keypad 44, a cassette receptacle 46 for a tube cassette containing an upstream pressure sensor 52 and a downstream pressure sensor 54, a motor (not shown) which rotates a pump wheel 56 with radial propulsion fins 56F positioned adjacent to the cassette receptacle 46 so that the fins 56F abut and drag against the delivery tube 20 to deform and propel the solution S within the tube 20, a tube cassette door 62 to close over the cassette receptacle 46, and a tube cassette 60 for releasably fitting into the cassette receptacle 46. The tube cassette 60 includes the downstream tubing segment 20B, the upstream tubing segment 20A, a feeding bag 30, a barbed enteral adaptor (not shown, an adaptor cover (not shown), a spike (not shown) and a spike protective cover (not shown). The INFINITY™ is adapted to become a part of the present apparatus 10 by removing or omitting from the delivery tube free end 22 the barbed enteral adaptor and spike and their covers, and replacing them with the present, inventive mouthpiece 80, and optionally a mister.

As noted, pole P preferably is part of an IV stand ST, and it has two diametrically opposing pole arms A extending horizontally outward from the top of pole P, so that pole P has a T-shaped configuration. See FIGS. 2, 4 and 6. Pole P is secured to a rolling base platform 200 formed of base cross-members 202, each cross-member 202 riding on a pivoting or castor base wheel 204 at its free end. The source bag 30 is suspended from an arm A extending from the pole P. The arm A free ends are curved back underneath to form arm hooks AH, and source bag 30 has a source bag mounting hole 32 in its upper end through which an arm hook AH is passed to suspend the bag 30. Delivery tube 20 is optionally fastened to a prong 180 extending from a prong clamp 160 secured to pole P, so that tube 20 extends substantially straight downwardly to a mouth of the user to prevent a user from becoming tangled in delivery tube 20. Delivery tube 20 preferably is fastened to prong 180 with a tie strip 184 having hook and loop fastener segments which are pressed together after the tie strip 184 is wrapped around tube 20 and prong 180. See FIGS. 3 and 5.

Prong clamp 160 preferably includes a generally C-shaped clamp body 170 made up of an elongate prong clamp anchoring block 172 and first and second block legs 174 and 176 for fitting around the pole P. First block leg 174 has a threaded passageway 174A extending horizontally and parallel to prong anchoring block 172. See FIGS. 15-17. A set-screw 178 is screwed into and through threaded passageway 174A and screwed against pole P, to releasably anchor prong clamp 160 to pole P. Set screw 178 preferably is fitted with a set screw dial 178A so that set screw 178 can be rotated by hand without a tool. A prong 180 is fitted into any one of the several prong holes 182 in block 172 to protrude laterally from prong clamp 160 and support the delivery tube 20 at an extended position from the pole P. This permits the tube 20 to be positioned more directly over the head of a user lying in a bed or sitting in a chair, so that the tube 20 extends directly down to the user mouth.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. An apparatus for delivering a metered stream of saliva solution, comprising:
    a delivery tube for drawing a saliva solution from a saliva solution source;
    a pumping and metering device connected to said delivery tube for pumping the saliva solution from the saliva solution source through said delivery tube and delivering the saliva solution to a user mouth, said delivery tube having a delivery tube upstream segment for extending from the saliva solution source to said pumping and metering device, and a delivery tube downstream segment extending from said pumping and metering device to a delivery tube free end for placement in the user mouth;
    and a mouthpiece mounted to said delivery tube free end for engaging and securely retaining said delivery tube free end within the user mouth until released;
    said mouthpiece comprising: a mouthpiece first panel having a first panel port, wherein said delivery tube free end passes through said first panel port and extends beyond said first panel, into the user mouth, wherein said delivery tube free end is releasably retained within said first panel port by a first tube engaging mechanism, such that said delivery tube free end can be placed within the user mouth and between upper and lower sets of user teeth, such that said retaining first panel extends radially outward from said tube between forward faces of user teeth and user lips, thereby holding said first panel and said delivery tube free end in the user mouth while obstructing movement of said delivery tube free end further into the user mouth when the user mouth is closed;
    a mouthpiece second panel having a second panel port, wherein said delivery tube free end passes through said second panel port and extends beyond said second panel, into the user mouth such that said second panel is spaced rearwardly of said first panel along said delivery tube to receive between said first panel and said second panel the user teeth, wherein said delivery tube free end is releasably retained within said second panel port by a second tube engaging mechanism, such that said delivery tube free end can be placed within the user mouth and between upper and lower sets of user teeth, such that said second panel extends radially outward from said tube behind rearward faces of user teeth, thereby holding said second panel and said delivery tube free end in the user mouth while obstructing movement of said delivery tube free end out of the user mouth when the user mouth is closed and when the user mouth is open, to deliver the saliva solution into the user mouth.

2. The apparatus of claim 1, wherein the saliva solution source is a source bag.

3. The apparatus of claim 1, wherein said first panel perimeter is substantially elliptical and sized such that when placed in the user mouth the ellipse short diameter extends generally parallel to the length of individual user teeth and terminates at first panel upper and lower ends short of making contact with user gums, while the ellipse long diameter extends laterally across user teeth forward faces for maximized first panel abutment area.

4. The apparatus of claim 1, wherein the outer diameter of said delivery tube free end is at least as great as the diameter of said first panel port through which said delivery tube free end passes, such that friction between said delivery tube and edges of said first panel port functions as said first tube engaging mechanism, releasably holding said first panel on said delivery tube.

5. The apparatus of claim 1, wherein said pumping and metering device comprises a pump for pumping the saliva solution through said delivery tube, a keypad for entering desired flow rate selection data into said pumping and metering device, and a display for showing selected flow rate data.

6. The apparatus of claim 1, additionally comprising a shut-off valve for starting and stopping the flow of the saliva solution through said delivery tube.

7. The apparatus of claim 6, wherein said shut-off valve comprises a resilient clip fitted around and compressing said delivery tube, thereby controlling flow through said delivery tube.

8. The apparatus of claim 3, wherein said second panel perimeter is substantially elliptical and sized such that when placed in the user mouth the ellipse short diameter extends generally parallel to the length of individual user teeth and terminates at second panel upper and lower ends short of making contact with user gums, while the ellipse long diameter extends laterally across user teeth rearward faces for maximized second panel abutment area.

9. The apparatus of claim 4, wherein the outer diameter of said delivery tube free end is at least as great as the diameter of said second panel port through which said delivery tube free end passes, such that friction between said delivery tube and edges of said second panel port functions as said second tube engaging mechanism, releasably holding said second panel on said delivery tube.

10. The apparatus of claim 1, wherein said first tube engaging mechanism additionally comprises at least two circumferentially spaced apart first panel radial slits extending outwardly from said first panel port to define resilient first panel sections, said resilient first panel sections resiliently bring against and gripping said delivery tube.

11. The apparatus of claim 10, wherein said second tube engaging mechanism additionally comprises at least two circumferentially spaced apart second panel radial slits extending outwardly from said second panel port to define resilient second panel sections, said resilient second panel sections resiliently bearing against and gripping said delivery tube.

* * * * *